United States Patent [19]

Sekido et al.

[11] 4,314,996
[45] Feb. 9, 1982

[54] OXYGEN SENSOR

[75] Inventors: Satoshi Sekido, Yawata; Kozo Ariga, Takatsuki, both of Japan

[73] Assignee: Matsushita Electric Industrial Company, Limited, Osaka, Japan

[21] Appl. No.: 136,404

[22] Filed: Apr. 1, 1980

[30] Foreign Application Priority Data

| Apr. 4, 1979 | [JP] | Japan | 54-40566 |
| Jun. 11, 1979 | [JP] | Japan | 54-73402 |
| Aug. 24, 1979 | [JP] | Japan | 54-108287 |
| Aug. 27, 1979 | [JP] | Japan | 54-108967 |
| Sep. 25, 1979 | [JP] | Japan | 54-122988 |

[51] Int. Cl.$^3$ ............................................. G01N 27/12
[52] U.S. Cl. .................................. 422/98; 338/34; 422/94
[58] Field of Search ............... 204/1 S, 195 S; 422/88, 422/98, 94; 338/34; 73/27 R

[56] References Cited

U.S. PATENT DOCUMENTS

| 3,400,054 | 9/1968 | Ruka et al. | 204/195 S |
| 3,558,280 | 1/1971 | Panson et al. | 422/98 |
| 3,751,968 | 8/1973 | Loh et al. | 422/98 |
| 3,922,204 | 11/1975 | Tseung et al. | 204/1 S |
| 3,951,603 | 4/1976 | Obayashi et al. | 338/34 X |
| 3,953,173 | 4/1976 | Obayashi et al. | 338/34 X |
| 3,955,929 | 5/1976 | Kawakami et al. | 422/88 |
| 4,130,797 | 12/1978 | Hattori et al. | 422/98 |
| 4,164,462 | 8/1979 | Ichikawa et al. | 204/195 S |
| 4,221,827 | 9/1980 | Parry et al. | 422/98 X |

FOREIGN PATENT DOCUMENTS

| 49-103699 | 10/1974 | Japan | 422/98 |
| 1081545 | 8/1967 | United Kingdom | 204/195 S |
| 1352995 | 5/1974 | United Kingdom | |

*Primary Examiner*—G. L. Kaplan
*Attorney, Agent, or Firm*—Lowe, King, Price & Becker

[57] ABSTRACT

An oxygen sensor element comprising a substrate made of a compound oxide of the perovskite type and a pair of electrodes electrically connected to the substrate. The compound oxide has a formula $ABO_3$ in which A represents an element of the lanthanum family, an alkaline earth metal or a mixture thereof and B is a transition metal.

11 Claims, 17 Drawing Figures

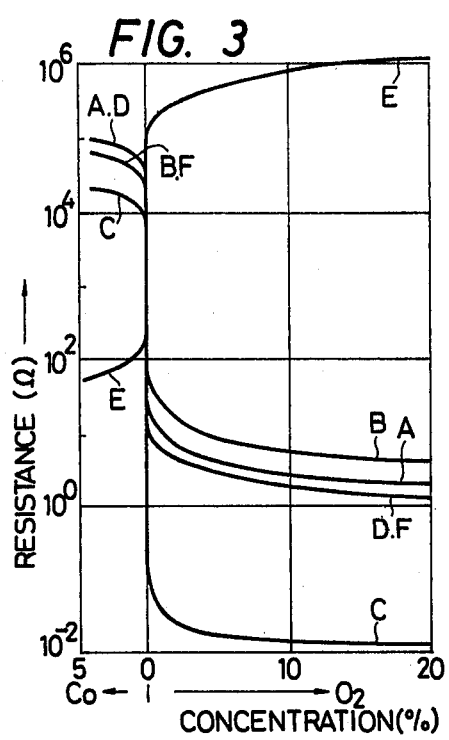
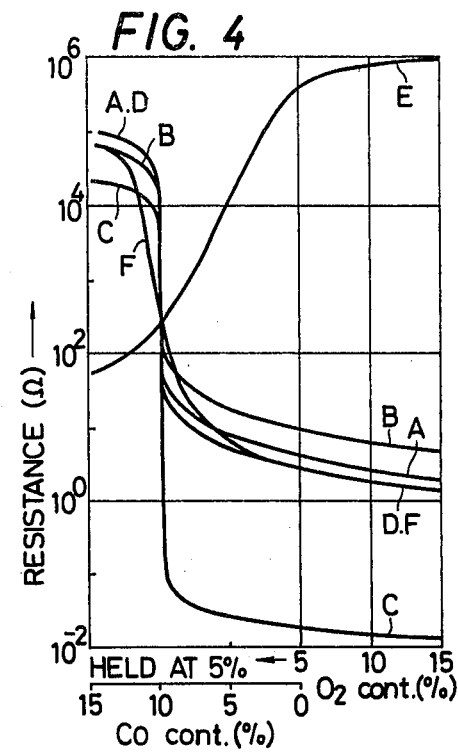
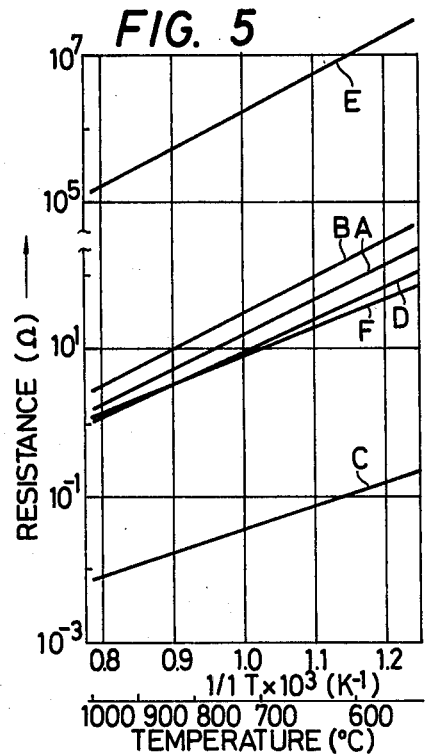
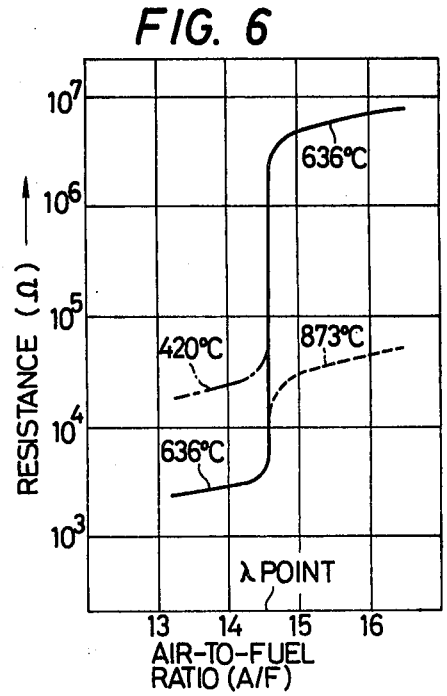

OXYGEN SENSOR

BACKGROUND OF THE INVENTION

Field of the Invention

This invention relates to an oxygen sensor and more particularly to, an oxygen sensor element in which the resistance of the element varies depending on a concentration of oxygen in a multicomponent gas environment.

In order to control the air-to-fuel ratio in a combustion system of automotive internal engines or in burners or to operate safety devices for preventing the incomplete combustion of gas or oil machinery and apparatus, there has recently been an increased demand for oxygen sensors which are inexpensive and highly reliable in performance.

Typical of commercially available oxygen sensors is an oxygen sensor which comprises a sensor substrate or base of a specific form composed of a solid electrolyte of stabilized zirconia and a pair of platinum electrodes disposed along the inner and outer surfaces of the substrate, respectively. In the sensor of the just-mentioned type, the concentration of oxygen in a gas mixture is detected as a change in electromotive force generated between the electrodes when a gas composition is changed. This sensor has an advantage that even though oxidative and reductive gases are both present in a gas environment to be measured, the chemical equilibrium reaction proceeds rapidly owing to the catalytic action of platinum used as the electrodes, so that an abrupt change of the electromotive force of the sensor takes place in the neighbourhood of the stoichiometric point of combustion of both types of gases. However, it is disadvantageously expensive since the platinum electrode is essential and the sensor has to be constructed in a complicated form.

Another type of oxygen sensor has been also proposed using a substrate constituted of $TiO_2$ or $MgCo_2O_4$, in which a variation in resistance of the substrate is utilized for detecting an oxygen concentration in a gas mixture. Though inexpensive, this sensor itself has no function as a catalyst for combustion and when it is used in an atmosphere of an exhaust gas where oxidative and reductive gases are present, its performance becomes unstable in the vicinity of the stoichiometric point of combustion. Thus, an abrupt change of the resistance at that point cannot be expected. In the cases of automotives and large-size steam power plants provided with three-way catalyst systems for converting harmful gases in exhaust gases into innoxious ones, satisfactory results are obtained when the sensor is placed in a passage of an exhaust gas which has been passed through the three-way catalyst system to undergo the chemical equilibrium reaction. However, combustion devices of small sizes which have no catalyst system encounter the problem mentioned above.

SUMMARY OF THE INVENTION

It is therefore an object of the present invention to provide an oxygen sensor element whose substrate is made of a material of a specific type which serves as a catalyst for combustion and has p-type semiconductive characteristics.

It is another object of the invention to provide an oxygen sensor element which shows a very low resistance in an atmosphere of oxidative gases but greatly increases in resistance in an atmosphere of reductive gases.

It is a further object of the invention to provide an oxygen sensor element in which the chemical equilibrium reaction proceeds rapidly in an atmosphere of a mixture of oxidative gases such as $NO_x$, $SO_x$, and $O_2$ and reductive gases such as hydrocarbons, CO and alcohols and the electrical resistance abruptly varies in the vicinity of a stoichiometric point ($\lambda=1$) of combustion of both types of gases.

It is a still further object of the invention to provide an oxygen sensor element which is inexpensive and simple in construction.

These and other objects, features and advantages of the invention will become apparent to those skilled in the art from the following description when taken in conjunction with the accompanying drawings and appended claims.

The oxygen sensor element in accordance with the present invention includes a base or substrate made of a compound oxide of the perovskite type and a pair of electrodes electrically connected to the substrate and spaced apart from each other, the compound oxide of the perovskite type having a formula $ABO_3$ where A represents an element of the lanthanum family, an alkaline earth metal or a mixture thereof and B represents a transition metal such as Fe, Co, Ni, Cr, Mn, Ra or Ir.

In a preferred embodiment, in the compound oxide of the formula $ABO_3$ A represents an element of the lanthanum family and B represents Co, Mn or a mixture thereof.

In another preferred embodiment according to the invention, the substrate is made of the compound oxide of the above-mentioned type and a minor amount of a glass material of high melting point dispersed in the compound oxide.

BRIEF DESCRIPTION OF THE DRAWINGS

FIGS. 3 and 4 are graphical representations of variations in resistance of the sensors according to the invention and also of known sensors using $TiO_2$ and $MgCo_2O_4$ as substrate in relation to variations in content of CO and $O_2$ of a gas environment;

FIG. 5 is a graphical representation of variations in resistance of sensor elements according to the invention in relation to temperature in an atmosphere containing 5% of oxygen;

FIG. 6 is a graphical representation of a resistance characteristic of a known gas sensor for automotive engines in relation to variation in air-to-fuel ratio for different temperatures;

DETAILED DESCRIPTION OF THE EMBODIMENTS

Figure 1:
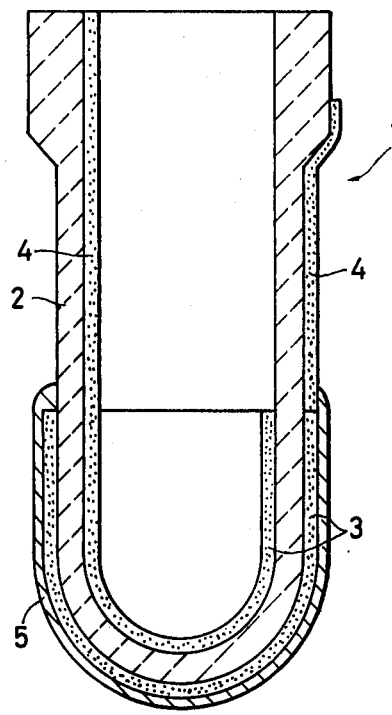
FIG. 1 is a schematical sectional view of a known oxygen sensor of the type in which an electromotive force of a stabilized $ZrO_2$ electrolyte is utilized.

In FIG. 1 there is shown a known oxygen sensor 1 which has been illustrated hereinbefore as typical of commercially available oxygen sensors and which includes a substrate or base 2 of a U shape in section. The substrate 2 is provided with platinum electrodes 3 along the inner and outer surfaces at a lower portion of the substrate 2, respectively. As mentioned hereinbefore, the sensor of this type makes use of an electromotive force produced between the electrodes 3 on variation of a gas composition to be measured. In this figure, indicated at 3 are leads of platinum foil, and at 4 is a protecting layer of porous $Al_2O_3$ for converting the electrode 3 on the outer surface. As mentioned, the sensor is relatively complicated in shape and uses a relatively large amount of platinum, and is thus expensive.

Figure 2:
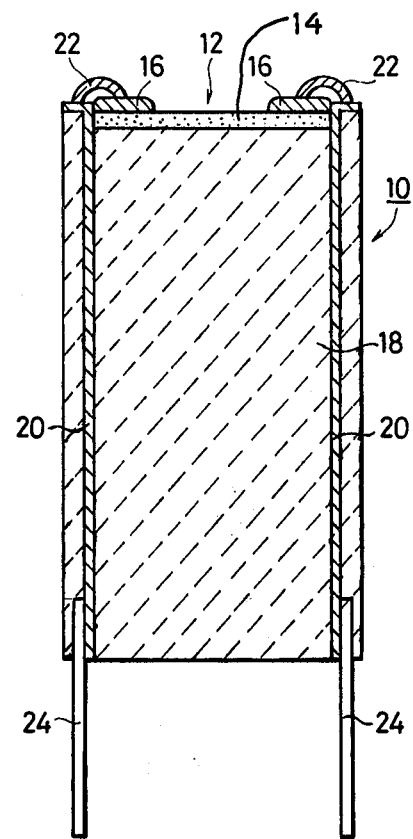
FIG. 2 is a schematical sectional view of an oxygen sensor using a sensor element embodying the present invention.

Referring to FIG. 2, there is shown an oxygen sensor using a sensor element according to one embodiment of the invention. The oxygen sensor generally indicated at 10 includes a sensor element 12 having a substrate 14 made of an oxide of the perovskite expressed by the formula $ABO_3$ in which A represents an element of the lanthanum family, an alkaline earth metal or a mixture thereof and B represents a transition metal such as Fe, Co, Ni, Cr, Mn, Ra or Ir, and a pair of electrodes 16 electrically connected to the substrate 14. In a preferred aspect, A of the formula represents an element of the lanthanum family, most preferably lanthanum and B represents Co, Mn or a mixture thereof.

The electrodes 16 are formed on the substrate 14, for example, by vacuum deposition or sputtering of a metal such as Pt, Pd, Au, Cr, C, Ni or W or by printing a conductive paste containing the metal and baking it. The sensor element 12 is disposed on a sintered alumina mount 18 which has leads 20 such as, for example, of W embedded in the mount 18. Each lead 20 is connected with a lead wire 22 at one end and a terminal 24 such as of Ni at the other end. Each lead wire 22 is electrically connected to the electrode 16 at the other end and is generally made of the same metal as used above.

The excellence of the oxygen sensor thus constructed in comparison with known counterparts will be illustrated with reference to FIGS. 3 through 5 in which A indicates an oxygen sensor using $LaCoO_3$ as an oxide material for the substrate, B indicates the sensor using a $Sr(Nb_{\frac{1}{2}}Co_{\frac{1}{2}})O_3$, C indicates a sensor that uses a $Sr_{1/5}La_{4/5}CoO$, D indicates a sensor using an $LaMnO_3$ substrate, E indicates a sensor that uses a known $TiO_2$ substrate and F indicates a sensor using a known $MgCo_2O_4$ substrate. All the samples are made by a press molding in a size of 2 mm wide×5 mm long×0.4 mm thick. The sintering temperature for $TiO_2$ alone is 1450° C. and that for the other is 1200° C.

FIG. 3 shows results of a test in which each sensor is placed in a quartz tube, maintained at a temperature of 850° C., through which a carrier gas of nitrogen admixed with 20% of oxygen at an initial stage is passed at a rate of about 1 m/sec and when a steady state is reached, a resistance of each sensor is measured. Then, while the content of oxygen is reduced stepwise, a steady resistance of each sensor is measured whenever the content is reduced. Subsequently, the content of oxygen is made zero and the content of CO gas is stepwise increased to measure a steady resistance at each step.

FIG. 4 shows results of a test in which a steady resistance of each sensor is measured such that when the content of oxygen reaches 5%, a content of CO gas is gradually increased while keeping the content of oxygen gas at 5%.

FIG. 5 shows results of a test in which a steady resistance of each sensor is measured while keeping a content of oxygen at 5% but changing the temperature.

As will be seen from FIGS. 3 and 4, in an atmosphere of a nitrogen gas to which either oxygen gas or CO gas is added singly, a logarithm of the concentration of the added gas continuously varies in proportion to a logarithm of the resistance. It is found from FIG. 3 that the resistances of any of oxides employed drastically vary at a point where the atmosphere is nitrogen gas alone. From FIG. 4 it is found that the sensors using the perovskite-type oxides according to the invention sharply vary in resistance at a stoichiometric point of oxygen and CO but such a sharp variation does not take place in the case of the known sensor using $TiO_2$ or $MgCo_2O_4$. It is believed that the variation of resistance in the case where either oxygen gas or CO gas is added to nitrogen gas occurs according to an ordinary theory of the valance control but the variation occurring at about a stoichiometric point is based on another mechanism. This is because to reach a stoichiometric point between an oxidative and a reductive gas is readily known from an abrupt variation in resistance at the point. Even though oxygen and a reductive gas such as Co are present in a mixed state such as in exhaust gases of an oxygen-lean state, the oxide of the perovskite type having a high catalytic action causes the equilibrium reaction to proceed rapidly and varies in resistance abruptly at about a stoichiometric point. Materials showing p-type semiconductivity such as the oxides of the perovskite type used in the practice of the invention and $MgCo_2O_4$ become lower in resistivity in an oxidative gas atmosphere than in a reductive atmosphere. This is contrary to the case of $TiO_2$. In both types of materials, there is a tendency that the speed of response becomes slow as the resistance varies from a low to high levels. This tendency becomes more pronounced when using a material which shows a greater variation of resistance. This is due to the fact that the element body may include a portion of high resistivity because of non-uniformity of the body but a portion of high resistivity is also present, so that an entire resistance of the element is kept constant. In order to prevent this, it is necessary not only to use a material which is uniform in quality but also to make the element body thin and small in width. When using dimensions of the element bodies shown in the foregoing, a delay of the response can be suppressed to below 1 minute.

It is desirable that the resistance of an element depends on a gas composition alone. In practice, however, it is inevitable that the resistance is dependent on the temperature as is clear from FIG. 5. No trouble is produced in detection if a variation in resistance of an element at a stoichiometric point exceeds that caused by the temperature. However, where the temperature dependency presents a problem, it is necessary to incorporate a thermister for compensation. Especially when a great variation of temperature (400° C.–900° C.) is involved as in exhaust gases of automobiles, it is the common practice to use a thermister of uniform characteristics in combination with a sensor element since the material itself of the sensor substrate suffers a great variation of temperature, leading to a disadvantage that a circuit for measurement becomes complicated with a high cost of the sensor.

In FIG. 6, there are shown curves of variations in resistance of a sensor using $TiO_2$ in an exhaust gas of automobile, which are plotted against an air-to-fuel ratio (A/F). In the figure, the variation of resistance at 636° C. is shown by a solid line, which is greatly different from that at 873° C. in a lean burn condition. That is, the resistance of the $TiO_2$ sensor at 873° C. in the lean burn state is at the same level as that at 420° C. under oxygen-rich conditions. since the temperature of the exhaust gas sharply varies within a range of the above-indicated temperatures, the resistance-A/F ratio curves of FIG. 6 indicate that error appears unless a temperature correction is made.

Since the oxides of the perovskite type used in the practice of the invention show only a small variation in resistance depending on the temperature, such a correction as needed in the known sensor is unnecessary. As a matter of course, it is easier to design an external circuit when a variation in resistance at λ point is greater. In this sense, the oxide materials used in the invention are superior to known ones because of their great variation in resistance in the order of five figures at high temperatures and in the order of seven to eight figures at low temperatures. Further, the oxide materials are low in resistivity as is different from known insulators or semiconductors and show approximately the same level of resistivity as a conductor of an external circuit in an atmosphere of oxidative gas. Accordingly, an oxygen sensor using such oxide materials consumes little or no electric power except that reductive gases are present in excess and can satisfy a requirement of fail safe on application to gas fittings for demostic purposes.

This will be particularly illustrated in detail with reference to an oxygen sensor using an oxide of the perovskite type of the formula $ABO_3$ in which A represents lanthanum and B represents cobalt, i.e. $LaCoO_3$.

First, a method of producing $LaCoO_3$ is described.

This compound is synthesized from lanthanum acetate and cobalt acetate. That is, equimolar quantities of these starting materials are weighed accurately and each dissolved in ion-exchanged water. The two solutions are placed in a container and sufficiently mixed, after which the solution is dehydrated and dried by a rotary evaporation. The dried substance is placed in an alumina crucible and gradually heated up to 500° C. in air. After the dehydration, the acetates are decomposed, part of which is oxidized. As a result, a pumice-like mass is formed. This is powdered and shaped in a desired form under a pressure of 500 kg/cm$^2$, followed by placing again in an alumina crucible for reaction at 900° C. for 2 hours in air or in an atmosphere of oxygen gas. After cooling, the resulting reaction product is ground to give a perovskite powder as a starting material.

The powder is mixed with 4 g of methyl cellulose and 2.5 ml of glycerine per 100 g of the powder, to which is added water. The mixture is well compounded to give a uniform paste. The paste is placed in an extrusion mold to make a rod of 2 mm in diameter. The rod is dried in air and cut into pieces of a suitable length, followed by calcining in air or oxygen gas. The calcination is effected as follows: The temperature is raised at a rate of about 500° C./hour to 850° C., at which it is maintained for 1 hour to decompose by oxidation methyl cellulose and glycerine incorporated as the binder. Then, the temperature is raised to 1100° C., at which it is maintained for 3 hours and the calcined pieces are cooled at a rate of 130° C./hour. Each sample is applied with a platinum paste in a desired manner and baked at about 1000° C. to give a sensor element attached with electrodes thereon.

Higher calcining temperatures result in higher mechanical strength but, at temperatures higher than 1300° C., sintering proceeds, which results in a delayed response of the element on measurement. Presumably, this is because interstices formed during the sintering serve as a passage for gas, giving an influence on a response speed.

This sensor element is connected with silver wires and its resistance is measured by placing the element in a quartz tube kept in an electric furnace while changing a gas composition of an environment.

The resistance at room temperature is very low and the element has a resistivity of $4 \times 10^{-2} \Omega$ cm when the volume corresponding to internal pores is corrected, and is thus a conductor. In this connection, it is possible to make a sensor element which has a resistance of about 10$\Omega$ by calcining a substrate under such conditions as to give relatively large-size, internal pores.

The sensor element which has been made under such calcining conditions as mentioned above is as low in resistance as or lower than a wiring of a measuring circuit.

Figure 7:
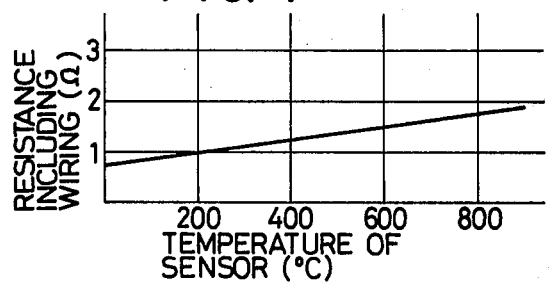
FIG. 7 is a graphical representation of a resistance of a sensor element according to the invention in relation to temperature in an atmosphere of air (having an $O_2$ content of 21%)

The resistance of the element including that of the wiring is measured in air under different temperature conditions, with the results shown in FIG. 7. Since samples with large pores show almost the same level of temperature coefficient at temperatures above 350° C., the relationship between the resistance and the temperature in FIG. 7 is believed to be a variation of resistance of the wiring depending on the temperature. From this it will be found that the sensor element according to the invention undergoes a much more reduced influence of temperature than known oxygen sensors.

Figure 8:
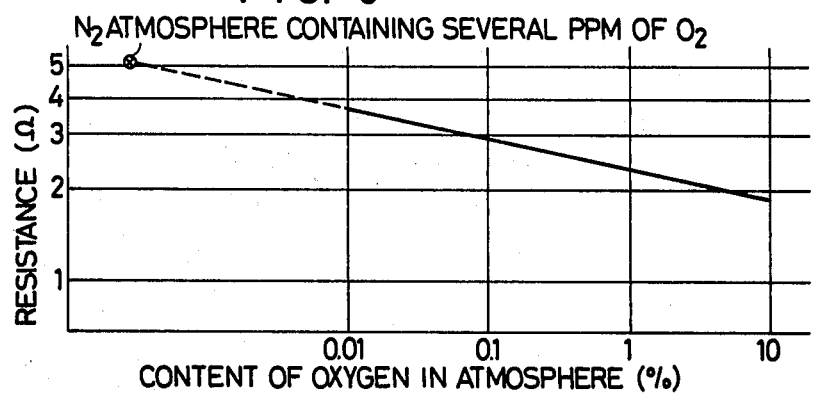
FIG. 8 is a graphical representation of a resistance of a sensor element according to the invention in relation to concentration of oxygen.

Then, a variation in resistance of the sensor element according to the invention is measured in atmospheres of gas where a content of oxygen is varied, with the results of FIG. 8 using an atmospheric temperature of 840° C. From this it will be appreciated though the resistance does not increase abruptly yet due to a slight amount of residual oxygen in nitrogen gas, the variation of the resistance depends on a variation of the concentration in defects of oxygen ions contained in the crystals.

Figure 9:
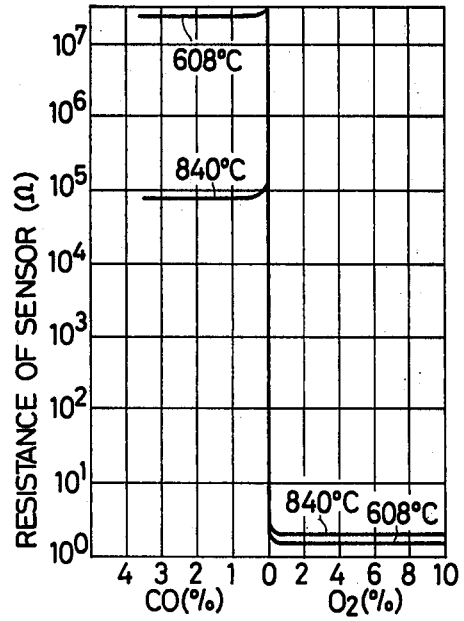
FIG. 9 is a characteristic graph showing a slight variation of resistance of an oxygen sensor element according to the invention in relation to concentrations of oxygen and carbon monoxide for different atmospheric temperatures.

When a resistance of the sensor according to the invention is measured in an atmosphere to which carbon monoxide(CO) is added as a reductive gas, a graph of FIG. 9 is obtained which is similar to that of FIG. 6. An abrupt variation in resistance takes place at a point, corresponding to the λ point of FIG. 6, where the oxidative and reductive gases are in an equilibrium. This variation becomes greater at lower temperatures. It will be noted that the variation of the resistance about 1 second just after changing from the oxidative atmosphere to the reductive atmosphere is in the order of three figures at 840° C. and in the order of about four figures at 608° C. and that the curves of FIG. 9 are obtained after a certain period of the atmospheric change. Accordingly, in the case where the sensor is applied to for the purpose of high speed response, the resistance variation becomes smaller than that shown in FIG. 9.

The speed of response becomes higher when the atmosphere changes from reductive to oxidative than from oxidative to reductive.

Any way, the variations of the resistance in FIG. 9 are much greater than those produced from $TiO_2$, leading to a presumption that they are different from each other in mechanism of the variation.

The X-ray analyses of the powder heated in air and the powder heated in reductive gas reveals that the perovskite is decomposed into a mixture of $La_2O_3$, and Co and $Co_2O_3$. From this it will be seen that the variation of resistance occurs as a result of the reduction reaction. When the produced powder is heated in an atmosphere of air, it is oxidized into the perovskite.

The variation of temperature in reductive atmosphere is negative in temperature coefficient and is thus coincident with that of FIG. 9 in the CO gas-containing atmosphere.

From the above, the excellency of the sensor characteristics of the element according to the invention will be understood and the practical utility of the element resides in a fact that the oxidation and reduction reactions proceed reversibly by changing the gas atmosphere from one type to the other.

As is clear from FIG. 9, the element shows p-type semiconductive characteristics in the oxidative gas but n-type characteristics in the reductive gas, which are attributed to $La_2O_3$ formed by the reaction.

When the sensor element which is connected to an external circuit for stopping a gas feed is disposed in an outer flame of a gas stove, it is found that it undergoes little or no variation in resistance over 3000 hours both at 600° C. and at 850° C. When a test is conducted in a closed space or system of the gas stove itself, the resistance of the element sharply increases at a concentration of oxygen of below about 18% and thus the external circuit works to close a valve of the gas and thus the fire is extinguished. The time required for the fire fighting is within 10 seconds and, in this condition, most of the substrate material is held as the perovskite. This is reflected by a fact that when the air in the closed space of the stove is replaced by fresh one and the stove is lit, the sensor instantaneously returns to a low resistance value.

The utility of the perovskite-type oxide as the sensor substrate will be understood from the foregoing, coupled with further advantages that it is easy to design an external circuit since the sensor using such substrate is low in resistance and that on breakage of the sensor, its resistance becomes so high as to satisfy the fail safe requirement, which is a great merit of the present invention as will not be experienced in prior-art sensors.

Though $LaCoO_3$ has been particularly described for use as a sensor substrate, similar results are obtained when using a similar type of perovskites of the formula $ABO_3$ in which A represents La, a lanthanide, an alkaline earth metal such as Ca, Sr or Ba or a mixture thereof and B represents Fe, Co, Ni, Cr, Mn, Ru or Ir, preferably Co or Mn. Examples of the oxide include $LaNiO_3$, $LaMnO_3$, $LaFeO_3$, $SrFeO_3$, $SrIrO_3$, $CaCrO_3$, $SrCrO_3$ and $LaCoO_3$, and those mentioned with reference to FIG. 3. Most preferably, $LaCoO_3$ is used. These oxides can be prepared in a manner similar to that described with regard to $LaCoO_3$.

Figure 10:
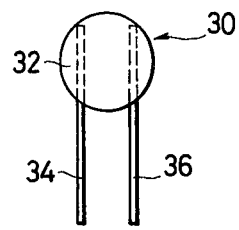
FIG. 10 is a schematical view of another embodiment according to the invention.

The sensor element may be shaped in any desired form depending on the purpose and end use. For instance, the element may be formed as shown in FIG. 10, which is generally indicated at 30 and includes a substrate 32 of a disc type and a pair of electrodes 34, 36 such as of platinum. This element can be made by applying a paste of a powder of a compound oxide of the perovskite to the paired electrode wires or charging the paste in a mold in which the electrodes wires are disposed, and then calcining the oxide mass or molding. The paste can be prepared by mixing the oxide powder, for example, with polyvinylbutyral, dioctyl phthalate and methyl alcohol in appropriate mixing ratios. The molding is calcined in air for example, at 1100° C. for 2 hours to obtain a sensor element. At the time of the calcining, the organic matters such as polyvinylbutyl incorporated in the slurry burn and are converted into carbon dioxide and water, so that the substrate 32 becomes porous, leading to a high speed of response as a sensor.

This sensor abruptly varies in resistance at a stoichiometric point of a relative concentration between oxygen and a reductive gas in an atmosphere of the gases. This abrupt variation is based on a fact that in the case of $LaCoO_3$, for instance, it undergoes in a reductive gas-rich atmosphere such a reaction that $LaCoO_3 \rightarrow La_2O_3 + Co$ and the reaction proceeds reversibly when the atmosphere is turned to an excess of oxygen. The magnitude of the variation at 830° C. is $10^5$ or more times. Though these reactions proceed reversibly, the contact resistance at the contact interface between the substrate and the electrode such as of platinum gradually increases. For instance, a total resistance of the sensor including a resistance of an external circuit in 4.53Ω at 830° C. After ten repetitions of the reduction and oxidation cycle, it increases up to 6.72Ω. We have found that the above increase results from a deterioration in contact between the electrodes and the substrate.

In order to keep the intimate electrical contact, it has been found effective to incorporate a glass powder in the oxide slurry prior to the molding of the element. By this, the glass acts to hold a strength of adhesion to the electrodes. It is known that a glass material may be used to improve the strength of an element in a gas sensor of the resistor type which is applied at low temperatures. In this connection, however, the gas sensor element for high temperature gas detection in accordance with the invention is different in working principle from the above-mentioned known sensor and a glass material is incorporated in the oxide paste so as to improve chiefly the contact with the electrodes, not the mechanical strength of the sensor element.

The glass material used should have a high melting point since the sensor element is used under high temperature conditions. In the practice of the invention, a glass material consisting of CaO, $SiO_2$ and $B_2O_3$ is used. The composition of such glass material is shown in Table below.

TABLE

| Component | Composition A | B |
|---|---|---|
| CaO | 64.0 wt % | 59.0 wt % |
| $B_2O_3$ | 26.0 | 35.0 |
| $SiO_2$ | 10.0 | 6.0 |

The composition A which contains a smaller amount of $B_2O_3$ has a melting point higher by about 100° C. than the composition B.

When the calcination is carried out at 1100° C., the glass A which has a melting point near the calcining temperature is suitably used, on which it is softened to improve an adhesion strength. With the glass B, similar results are obtained when using a calcining temperature of about 1000° C. By the incorporation of the glass there is no tendency toward increasing the resistance of an element on repetition of an oxidation and reduction cycle as will be experienced in a glass-free element.

The incorporation of the glass material of high melting point results in a highly effective porosity and thus the catalytic activity of the oxide effectively acts on a gas to be measured, improving the speed of response to the gas. As a matter of course, a glass material is not critically limited to those mentioned above but any glass materials having high melting points are likewise usable. The glass material is generally incorporated in an amount of below 30 wt% of the oxide of the pervoskite type.

The melting point of the glass material to be admixed should be equal to or higher than temperatures of calcination after molding. Otherwise, the molded element may be deformed.

Figure 11:
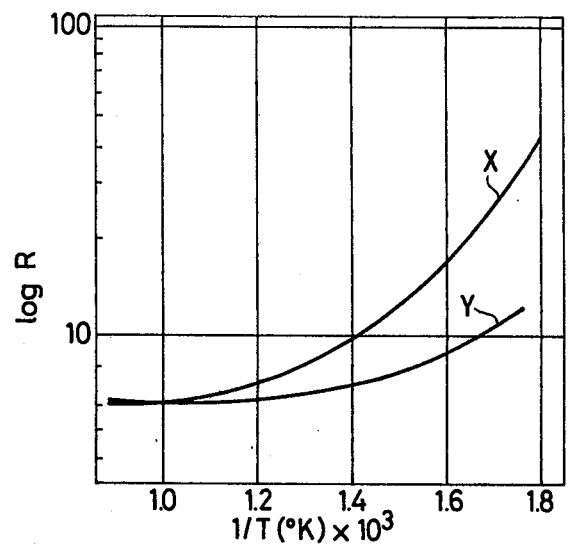
FIG. 11 is a graphical representation of a resistance-temperature characteristic of a sensor element using a glass-dispersed substrate according to the invention in relation to time.

It has been found that where a glass material as mentioned above is added to a compound oxide of the perovskite type, the resulting element shows a resistance characteristic which varies with time. This is particularly shown in FIG. 11. When a sensor element using a glass material which shows an initial resistance characteristic as shown by curve X of FIG. 11 is maintained at 850° C. for 8 hours, the characteristic curve obtained is as shown by curve Y. As is clearly seen from the figure, the resistance at low temperatures considerably decreases due to the incorporation of the glass and the resistance at 850° C. increased by about 0.1Ω. This element is obtained by calcining the oxide substrate at 1100° C. for 2 hours. Because of such a short time of calcination, the glass material is believed to become low in resistance when the element is held at a high temperature of 850° C. The lowering of the resistance at low temperatures is rather favorable in view of the fact that the element shows less temperature dependency. However, even though very small, an increase of the resistance at high temperatures is rather unfavorable from the viewpoint of stability and reliability of the element. The X-ray microanalysis or X-ray analysis reveals that such a variation of the resistance of the element is due to, when using $La_{1-x}Sr_xCoO_3$ as the oxide, diffusion of Co into the glass material and formation of $La_2O_3$ and $SrCo_3$ in excess.

In order to improve the resistance characteristic, an extensive study has been made and, as a result, it has been found that the glass material is preferred to be one which contains the same transition metal component as of the perovskite-type oxide used. This is particularly described with regard to $LaCoO_3$.

It will be noted that in order to lower the resistance of an element in an oxygen-rich condition, it is sufficient to substitute part of La with Sr or the like but since it is not necessary to make the resistance lower than a resistance of an external circuit constituting the sensor, $LaCoO_3$, is used.

In this case, $LaCoO_3$ is prepared from $La_2O_3$ and $Co_2O_3$. These starting materials are sufficiently wet mixed, to which methyl cellulose and water are added to give a paste. Then, the paste is placed in a mold and shaped in the form of a disc under a pressure of 300 $kg/cm^2$. The disc is heated and calcined at 1000° C. for 5 hours and wet ground to be a particle size of below 0.2 $\mu$m. This powder is one of one of the starting materials.

A glass material should withstand high temperature and must have a high melting point. Accordingly, a base material composed of 65 wt% of CaO, 26 wt% of $B_2O_3$ and 10 wt% of $SiO_2$ is used, to which $Co_2O_3$ is added in an amount of 5 parts by weight per 100 parts by weight of the glass. The mixture is heated to 1350° C. and maintained at the same temperature for 5 hours to formulate a uniform composition, followed by cooling and milling to give an auxiliary glass material.

The auxiliary glass material is generally added to the oxide material in an amount of 20 to 30 parts by weight per 100 parts of the oxide.

The auxiliary glass material is added to and sufficiently mixed with the compound oxide, followed by adding polyvinylbutyral, an alcohol and a small amount of DOP to give a slurry. The slurry is applied to so that it lies over two platinum electrodes which are spaced from each other, dried and then calcined in air at 1100° C. for 2 hours to give a sensor element as shown in FIG. 10. That is, this element is the same as that used for measurement of FIG. 11 except for the glass composition.

Figure 12:
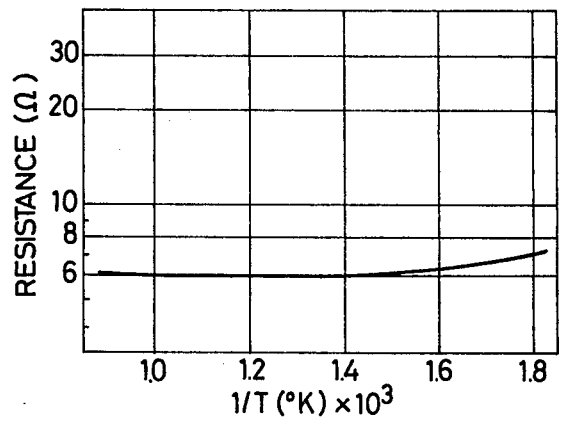
FIG. 12 is a graphical representation of a resistance-temperature characteristic of a sensor element according to the invention using a substrate which comprises a glass material containing the same type of a transition metal as in a compound oxide of the perovskite type.

The variation of resistance of the element in relation to temperature is shown in FIG. 12. This curve is an initial resistance variation against temperature but no change takes place after the element is thermally treated at 350° C. for 72 hours.

As is clear from FIG. 12, when incorporating in the compound oxide a glass material to which a compound containing the same transition metal as that of the compound oxide is added, the characteristic of the element is remarkably stabilized and the element is improved in stability against temperatures since its resistance at low temperatures is reduced.

In the above, Co is incorporated as a transition metal component in the glass material composed of CaO, $B_2O_3$ and $SiO_2$ since $LaCoO_3$ is used as the compound oxide but similar results are obtained when using a compound of the same transition metal as contained in a compound oxide employed. The transition metal is usually used in the form of an oxide, and is employed in such an amount as not to exceed a limit of forming a solid solution with the glass material and is generally in the range of 1 to 10% by weight of the glass material on the basis of a transition metal oxide.

It will be noted that in a gas sensor which is applied at low temperatures of below 500° C., a coefficient of diffusion of a metal element into a glass is small and thus the effect of the incorporation of such metal does not develop within a short time but a transition metal added to the glass material gives a favorable effect for the purpose of regulating an electric resistance of the sensor element under high temperature conditions.

As described hereinbefore, when $LaCoO_3$ or $La_{1-x}Sr_xCoO_3$ in which part of La is substituted with an alkaline earth metal is placed in a reductive gas-rich atmosphere or in a rich burn region under high temperature conditions over a long time, it is decomposed into $La_2O_3$ and Co in the case of $LaCoO_3$. This reaction reversibly proceeds and $LaCoO_3$ or $La_{1-x}Sr_xCoO_3$ is again formed when the atmosphere is returned to a lean burn state. This reversible reaction results in a very great variation of resistance which is useful as a sensor element. In practical applications, however, the reversible reaction involves a secondary ill effect that a contact resistance increases due to a deterioration in contact between the electrode and the oxide substrate. This disadvantage has been overcome in the foregoing by incorporating a Co-containing glass material in the compound oxide.

Figure 13:
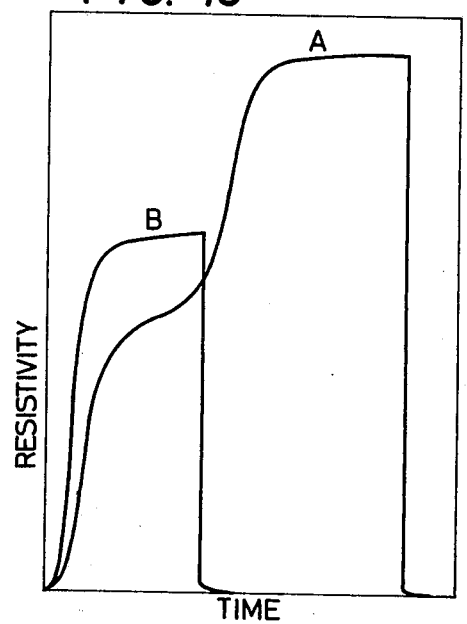
FIG. 13 is a graphical representation of resistivities of oxygen sensor elements using $LaCoO_3$ and $LaMnO_3$, respectively, in relation to time.

The resistance of a sensor element made of $LaCoO_3$ under oxidative gas-rich conditions varies with a time as schematically indicated by A of FIG. 13 with two inflection or saturation points. In a region ranging below the first inflection point where a variation of the resistance is in the order of as small as two figures, no contact deterioration is observed around the electrodes. Hence, the sensor element is applicable to any combustion systems such as a gas fitting without troubles when operated in a range of resistance below the first inflection point.

On the other hand, with $LaMnO_3$ wherein Co of $LaCoO_3$ is replaced by Mn, a variation of resistance in relation to time is simple as schematically indicated by B of FIG. 13.

$LaMnO_3$ which is prepared from $La_2O_3$ and $MnO_2$ as starting materials has a monoclinic structure of the perovskite type and a lattice constant of 5.471 Å. A sensor element using $LaMnO_3$ alone is higher in resistance than that of $LaCoO_3$ of the same size and is small in variation of resistance when exposed to a rich and lean burn cycle, i.e. the magnitude of the variation is about 3 times. Even when allowed to stand over a long time in a reductive atmosphere, the $LaMnO_3$ sensor element shows little or no deterioration in contact between the electrode and the substrate as is experienced with the $LaCoO_3$ element and is thus vary stable.

The X-ray analysis demonstrates that $LaMnO_3$ is not decomposed in a reductive atmosphere or in a rich burn condition and the perovskite structure does not change at all though an expansion of lattices is observed. Presumably, this is why the element is stable.

Then, we have made a further study of material which has both the low resistivity and great variation of resistance of $LaCoO_3$ and the stability of $LaMnO_3$ under rich burn conditions, and prepared compound oxides of the formula, $LaMn_{1-x}Co_xO_3$, in different values of x.

Figure 14:
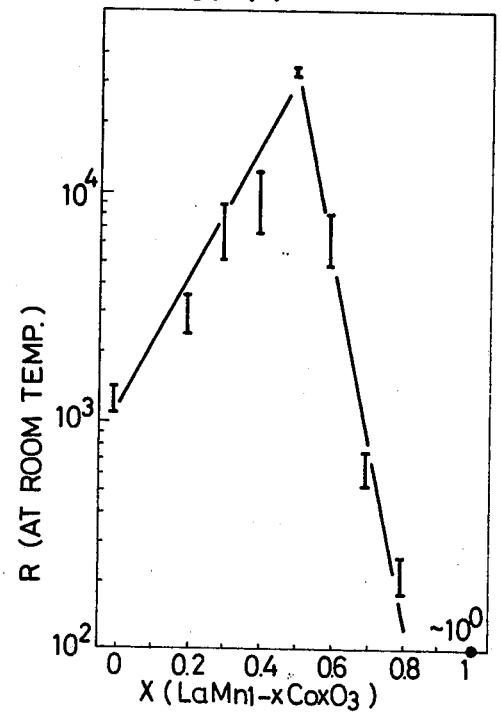
FIG. 14 is a graphical representation of a resistance of an oxygen sensor element according to the invention in relation to a composition of $LaMn_{1-x}Co_xO_3$.

FIG. 14 is a graph of resistances at room temperature of sensors using the compound oxides of different values of x. In the figure, range of a resistance at each x is indicated by a vertical line of a certain length and is ascribed to dispersions of a volume and a size of pores of a substrate produced on calcination.

As is clear from FIG. 14, the resistance sharply increases when x decreases to 0.5. However, when a content of Mn is increased further, the resistance again decreases. The crystal structure of these oxides except for an oxide of x=0 or $LaMnO_3$ are similar to that of $LaCoO_3$. Accordingly, the variation of the resistance is not ascribed to a phase variation of crystals. With x=0.5, the resistance of the sensor decreases with an increase of temperature and is below 30Ω at 850° C. In particular, the resistance of a sensor using the compound oxide where x=0.6 or greater is below 1Ω at 850° C. In this connection, the variation of resistance at temperatures greater than 400° C. is small and the element does not show any substantial change by temperature. In this sense, x is preferred to be not smaller than 0.6, though the oxide of the formula where x is any value of from 0 to 1 is usable.

On the other hand, the resistance of the sensor element in a combustion gas varies at an equivalence point of the gas composition. The ratio of a resistance under rich conditions to a resistance under lean conditions greatly depends on the value of x.

Figure 15:
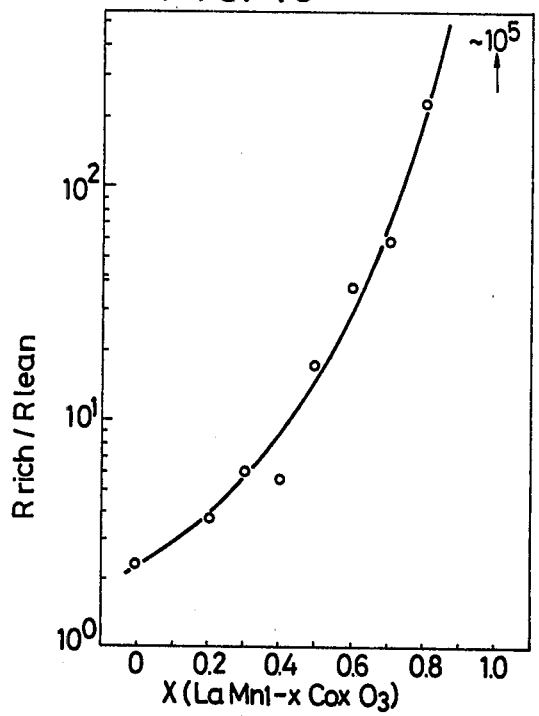
FIG. 15 is a graphical representation of a ratio of a resistance under oxygen-rich burn conditions to a resistance under oxygen-lean burn conditions in relation to a composition of $LaMn_{1-x}Co_xO_3$.

This is clearly shown in FIG. 15. As x increases, a variation of the resistance from a lean burn condition to a rich burn condition greatly increases. From this it will be seen that in order to increase the resistance ratio, x is preferred to be great. At high temperatures of about 850° C., the variation of resistance in relation to time is a curve showing only one inflection or saturation point when $x \leq 8$.

From the above, it has been found that the compound oxide of the formula $LaMn_{1-x}Co_xO_4$ where x=0.6–0.8 is suitable for the purpose of the invention. In other words, $LaMn_{1-x}Co_xO_3$ where x is in the range of 0.6 to 0.8 has a number of advantages that its resistivity is below 1Ω cm, that the resistance of the sensor using such oxide shows substantially no change at temperatures between 400° C. and 850° C., and that its variation of resistance becomes drastic at a stoichiometric point of reductive and oxidative gases.

Figure 16:
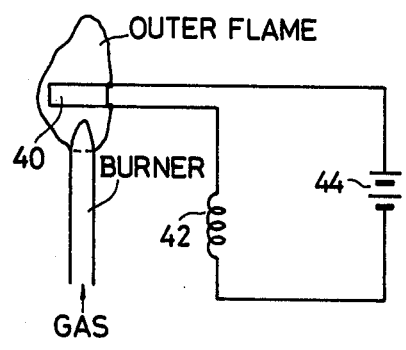
FIG. 16 is a schematical electric circuit diagram of a safety device to which an oxygen sensor element according to the invention is applied so as to prevent incomplete combustion of a gas fitting.

The oxygen element according to the invention has p-type semiconductor characteristics and, when applied to a combustion system, it can detect an oxygen-lean state and acts to turn a gas valve off by a simple circuit as shown in FIG. 16, in which an oxygen sensor 40 is connected to a safety valve 42 at one terminal and also to a cell 44 at the other. The sensor is placed in an outer flame of the combustion system. When incomplete combustion takes place, the resistance of the sensor 40 abruptly varies and such information is fed back to turn gas valve (not shown) off.

Figure 17:
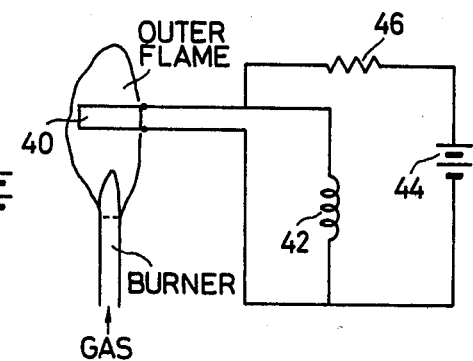
FIG. 17 is a schematical electric circuit diagram of a safety device for incomplete combustion using a known n-type oxide such as $TiO_2$.

In case where a $TiO_2$ oxygen sensor is used, it is necessary to use an external circuit which is more complicated than that required for the sensor according to the invention. In FIG. 17, a resistor 46 is series connected to the cell 44. This circuit is disadvantageous in that when the circuit is disconnected, it can not ensure fail safe of the combustion system.

What is claimed is:

1. An oxygen sensor element of the resistance type comprising a substrate made of a ceramic and a pair of electrodes electrically connected to said substrate and spaced apart from each other, said ceramic comprising: a powder of a compound oxide of the perovskite type having the formula $ABO_3$ in which A represents an element of a lanthanum family, an alkaline earth metal or a mixture thereof and B represents a transition metal, and a glass material which has a melting point equal to or higher than the temperature of calcination of the ceramic, and containing about 1 to 10 wt% of an oxide of the transition metal used, the glass material being contained in an amount of about 20 to 30 parts by weight per 100 parts of the compound oxide; whereby said oxygen sensor element varies in resistance abruptly in the vicinity of a stoichiometric point of reducing and oxidizing gases when said oxygen sensor element is placed in an atmosphere at elevated temperature and is normally stabilized in resistance below the elevated temperature conditions, whereby a concentration of the oxidizing gas is stably detectable.

2. An oxygen sensor element according to claim 1 wherein A represents the element of the lanthanum family and B represents Co.

3. An oxygen sensor element according to claim 1, wherein said compound oxide is $LaCoO_3$.

4. An oxygen sensor element according to claim 1 wherein said compound oxide is $LaMn_{1-x}Co_xO_3$ in which x is in the range of from 0 to 1.

5. An oxygen sensor element according to claim 4 wherein x is in the range of from 0.6 to 0.8.

6. An oxygen sensor element according to claim 1 wherein the substrate comprises a ceramic obtained by calcining a powder of the compound oxide of the perovskite type.

7. An oxygen sensor element according to claim 1 wherein the glass material is composed of CaO, $SiO_2$ and $B_2O_3$.

8. An oxygen sensor according to claim 1 wherein the transition metal oxide is $Co_2O_3$ and the compound oxide is $LaCoO_3$.

9. An oxygen sensor element according to claim 1 wherein the substrate has a resistance of below $1\Omega$ at temperatures of 400° C. or more.

10. An oxygen sensor element according to claim 1 wherein A represents a mixture of lanthanum and strontium.

11. An oxygen sensor element according to claim 1 wherein B represents Co, Mn or a mixture thereof.

* * * * *